(12) United States Patent
Cox

(10) Patent No.: US 6,766,200 B2
(45) Date of Patent: Jul. 20, 2004

(54) MAGNETIC COUPLING ANTENNAS FOR IMPLANTABLE MEDICAL DEVICES

(75) Inventor: Timothy J. Cox, Friendswood, TX (US)

(73) Assignee: Pacesetter, Inc., Sylmar, CA (US)

( * ) Notice: Subject to any disclaimer, the term of this patent is extended or adjusted under 35 U.S.C. 154(b) by 422 days.

(21) Appl. No.: 10/002,798

(22) Filed: Nov. 1, 2001

(65) Prior Publication Data

US 2003/0083718 A1 May 1, 2003

(51) Int. Cl.⁷ .................................................. A61N 1/02
(52) U.S. Cl. ...................................................... 607/60
(58) Field of Search ............................. 607/32, 59, 60; 128/899, 903, 904; 338/66

(56) References Cited

U.S. PATENT DOCUMENTS

| | | | |
|---|---|---|---|
| 4,561,443 A | 12/1985 | Hogrefe et al. | |
| 4,681,111 A | * 7/1987 | Silvian ........................ | 607/59 |
| 5,057,812 A | * 10/1991 | Yukawa et al. ............... | 338/66 |
| 5,058,581 A | 10/1991 | Silvian | |
| 5,113,869 A | 5/1992 | Nappholz et al. | |
| 5,342,408 A | 8/1994 | deCoriolis et al. | |
| 5,354,319 A | 10/1994 | Wyborny et al. | |
| 5,381,798 A | 1/1995 | Burrows | |
| 5,454,838 A | 10/1995 | Vallana et al. | |
| 5,496,351 A | 3/1996 | Plicchi et al. | |
| 5,496,361 A | 3/1996 | Moberg et al. | |
| 5,511,553 A | 4/1996 | Segalowitz | |
| 5,518,001 A | 5/1996 | Snell | |
| 5,544,661 A | 8/1996 | Davis et al. | |
| 5,562,713 A | 10/1996 | Silvian | |
| 5,617,871 A | 4/1997 | Burrows | |
| 5,674,249 A | 10/1997 | de Coriolis et al. | |
| 5,683,432 A | * 11/1997 | Goedeke et al. ............. | 607/32 |
| 5,697,958 A | 12/1997 | Paul et al. | |
| 5,720,770 A | 2/1998 | Nappholz et al. | |
| 5,748,103 A | 5/1998 | Flach et al. | |
| 5,752,976 A | 5/1998 | Duffin et al. | |
| 5,843,139 A | 12/1998 | Goedeke et al. | |
| 5,855,550 A | 1/1999 | Lai et al. | |
| 5,861,019 A | 1/1999 | Sun et al. | |
| 5,904,708 A | 5/1999 | Goedeke | |
| 5,944,659 A | 8/1999 | Flach et al. | |
| 5,999,848 A | 12/1999 | Gord et al. | |
| 6,004,276 A | 12/1999 | Wright et al. | |
| 6,009,350 A | 12/1999 | Renken | |
| 6,083,248 A | 7/2000 | Thompson | |
| 6,115,636 A | 9/2000 | Ryan | |
| 6,155,267 A | 12/2000 | Nelson | |
| 6,162,180 A | 12/2000 | Miesel et al. | |
| 6,200,265 B1 | 3/2001 | Walsh et al. | |
| 6,213,942 B1 | 4/2001 | Flach et al. | |
| 6,225,901 B1 | 5/2001 | Kail, IV | |
| 6,230,049 B1 | 5/2001 | Fischell et al. | |
| 6,234,973 B1 | 5/2001 | Meador et al. | |
| 6,238,492 B1 | 5/2001 | Nakanishi et al. | |
| 6,240,317 B1 | 5/2001 | Villaseca et al. | |
| 6,264,614 B1 | 7/2001 | Albert et al. | |
| 6,270,457 B1 | 8/2001 | Bardy | |
| 6,282,441 B1 | 8/2001 | Raymond et al. | |
| 6,301,504 B1 | 10/2001 | Silvian | |
| 6,312,378 B1 | 11/2001 | Bardy | |
| 6,315,721 B2 | 11/2001 | Schulman et al. | |

\* cited by examiner

*Primary Examiner*—George Manuel

(57) ABSTRACT

An implantable medical device is equipped with a magnetic coupling assembly to transfer communication signals to and from the device using electromagnetic energy.

45 Claims, 10 Drawing Sheets

MAGNETIC COUPLING ANTENNAS FOR IMPLANTABLE MEDICAL DEVICES

TECHNICAL FIELD

The present invention generally relates to implantable medical devices.

BACKGROUND

There are many kinds of implantable medical devices. Some monitor patient conditions while others disperse some form of therapy. One particular type of implantable medical device is an implantable cardiac therapy device, or ICTD. ICTDs are implanted within the body of a patient to monitor, regulate, and/or correct heart activity. ICTDs include implantable cardiac stimulation devices (e.g., implantable cardiac pacemakers, implantable defibrillators) that apply stimulation therapy to the heart as well as implantable cardiac monitors that monitor heart activity.

Implanted medical devices are typically capable of being programmed remotely by an external programming device, often called a "programmer". Individual ICTDs, for example, are equipped with telemetry circuits that communicate with the programmer. One type of programmer utilizes an electromagnetic wand that is placed near the implanted cardiac device to communicate with the implanted device. When used in a sterile field, the wand may be enclosed in a sterile sheath. The wand contains a coil that forms a transformer coupling with the ICTD telemetry circuitry. The wand transmits low frequency signals by varying coil impedance.

Early telemetry systems were passive, meaning that the communication was unidirectional from the programmer to the implanted device. Passive telemetry allowed a treating physician to download instructions to the implanted device following implantation. Due to power and size constraints, early commercial versions of implanted devices were incapable of transmitting information back to the programmer. As power capabilities improved, active telemetry became feasible, allowing synchronous bi-directional communication between the implanted device and the programmer. With improved processor and memory technologies, the implanted devices have become increasingly more sophisticated, allowing them to monitor many types of conditions, store the conditions and upload them to the programmer, and apply tailored therapies in response.

Current telemetry systems have a limited communication range between the programmer wand and the ICTD, which is often referred to as "short-range telemetry" or "wand telemetry". For effective communication, the wand is held within two feet of the ICTD, and more typically within several inches. One limitation is that the ICTD lacks sufficient power to transmit longer range signals. Another limitation is the slow speed at which data is transferred. Data is commonly transferred at less than one KByte/second. Holding a wand in place or strapping it to a patient for a minute or more is not considered expedient for medical personnel.

These shortcomings—short transmission distance and limited speed—can be overcome by adoption of radio frequency techniques of communication. Although being an established medium of communication, use of radio frequency techniques is not as easy as it might seem. One problem is that RF energy is not easily transmitted out of a patient's body. The patient's body tissue inhibits transmission by absorption of the emitted energy. The radio transmitter further requires an antenna having at least one dimension that is a significant fraction of a wavelength of the electromagnetic energy being emitted. Since size matters for implanted devices, the antenna size and structure is a significant factor to consider.

Furthermore, the implanted device is hermetically sealed in a metal enclosure or "can" that prevents penetration of electromagnetic energy of high frequency. The metal can limits communication to the low frequency range of less than 200 KHz. In one exemplary system, signals sent from the programmer to the implanted device are transmitted at approximately 36 KHz, and data is transmitted back from the implanted device to the programmer at approximately 8 KHz.

Accordingly, there is an ongoing need to improve the communication capabilities between implanted devices and external devices, and particularly the need to communicate more effectively over greater transmissions ranges.

SUMMARY

An implantable medical device is equipped with a magnetic coupling assembly to transfer communication signals to and from the device using electromagnetic energy. Two representative implementations are disclosed: a toridcoupled lead antenna and an inductive feed-through. The assemblies transfer electromagnetic energy between internal device circuitry and an external antenna (e.g., a lead or dedicated antenna). The assemblies effectively extract high-frequency data from the antenna while preventing high-frequency emanations from disrupting the internal device circuitry.

DETAILED DESCRIPTION

The following discussion unfolds in the context of an implantable cardiac therapy device (ICTD) linked to a networked system of computing systems. It is noted that the ICTD is just one exemplary type of implantable medical device. Other types of implantable medical devices may be employed, such as implantable medicine dispensers, implantable nerve stimulators, and so on.

Cardiac Therapy Network

Figure 1:
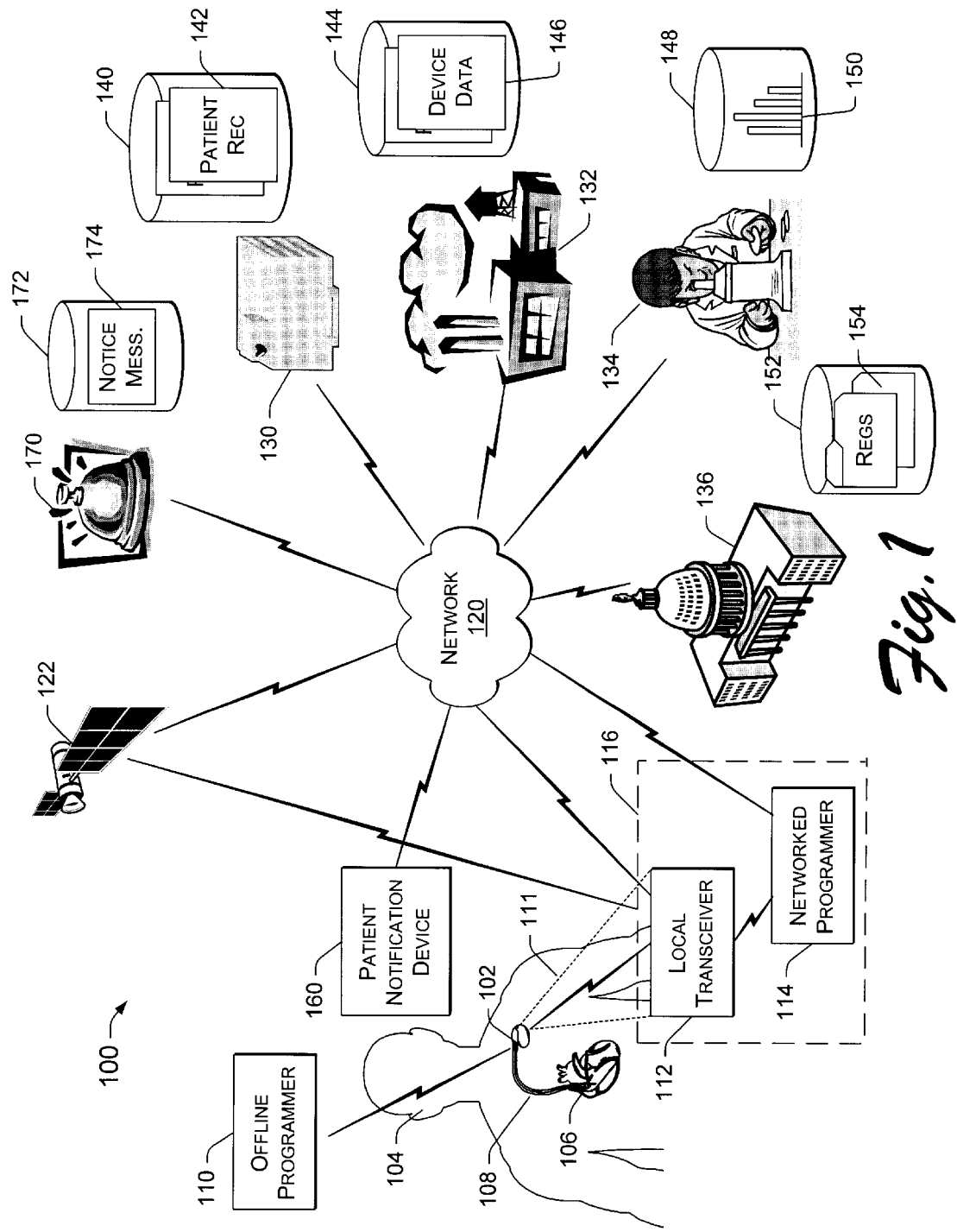
FIG. 1 is a diagrammatic illustration of a network architecture with an exemplary implantable medical device connected to a network of computing systems used by various knowledge workers. The implantable medical device is depicted and described in the context of an implantable cardiac therapy device (ICTD).

FIG. 1 shows an exemplary cardiac therapy network architecture 100 that includes an implantable medical device in the form of an implantable cardiac therapy device (ICTD) 102. The ICTD 102 is coupled to a network of computing systems associated with various knowledge workers who have interest in cardiac therapy. The ICTD is illustrated as being implanted in a human patient 104. The ICTD 102 is in electrical communication with a patient's heart 106 by way of multiple leads 108 suitable for monitoring cardiac activity and/or delivering multi-chamber stimulation and shock therapy.

The ICTD 102 may communicate with a standalone or offline programmer 110 via short-range telemetry technology. The offline programmer 110 is equipped with a wand that, when positioned proximal to the ICTD 102, communicates with the ICTD 102 through a magnetic coupling.

The ICTD 102 can alternatively, or additionally, communicate with a local transceiver 112. The local transceiver 112 may be a device that resides on or near the patient, such as an electronic communications device that is worn by the patient or is situated on a structure within the room or residence of the patient. The local transceiver 112 communicates with the ICTD 102 using short-range telemetry or longer-range high-frequency-based telemetry, such as RF (radio frequency) transmissions. Alternatively, the local transceiver 112 may be incorporated into the ICTD 102, as represented by dashed line 111. In this case, the ICTD includes a separate and isolated package area that accommodates high-frequency transmissions without disrupting operation of the monitoring and stimulation circuitry.

Depending upon the implementation and transmission range, the local transceiver 112 can be in communication with various other devices of the network architecture 100. One possible implementation is for the local transceiver 112 to transmit information received from the ICTD 102 to a networked programmer 114, which is connected to network 120. The networked programmer 114 is similar in operation to standalone programmer 110, but differs in that it is connected to the network 120. The networked programmer 114 may be local to, or remote from, the local transceiver 112; or alternatively, the local transceiver 112 may be incorporated into the networked programmer 114, as represented by dashed line 116.

Another possible implementation is for the local transceiver to be connected directly to the network 120 for communication with remote computing devices and/or programmers. Still another possibility is for the local transceiver 112 to communicate with the network 120 via wireless communication, such as via a satellite system 122.

The network 120 may be implemented by one or more different types of networks (e.g., Internet, local area network, wide area network, telephone, cable, satellite, etc.), including wire-based technologies (e.g., telephone line, cable, fiber optics, etc.) and/or wireless technologies (e.g., RF, cellular, microwave, IR, wireless personal area network, etc.). The network 120 can be configured to support any number of different protocols, including HTTP (HyperText Transport Protocol), TCP/IP (Transmission Control Protocol/Internet Protocol), WAP (Wireless Application Protocol), Bluetooth, IEEE 802.11, and so on.

A number of knowledge workers are interested in data gathered from the implantable cardiac therapy device 102. Representative knowledge workers include healthcare providers 130, the device manufacturer 132, clinical groups 134, and regulatory agencies 136. The knowledge workers are interested in different portions of the data. For instance, the healthcare providers 130 are interested in information pertaining to a particular patient's condition. The manufacturer 132 cares about how the device is operating. The clinical groups 134 want certain data for inclusion in patient populations that can be studied and analyzed. The regulatory agencies 136 are concerned whether the devices, and various treatments administered by them, are safe or pose a health risk.

The network architecture 100 facilitates distribution of the device data to the various knowledge workers. Information gathered from the device is integrated, processed, and distributed to the knowledge workers. Computer systems maintain and store the device data, and prepare the data for efficient presentation to the knowledge workers. The computer systems are represented pictorially in FIG. 1 as databases. However, such system can be implemented using a wide variety of computing devices, ranging from small handheld computers or portable digital assistants (PDAs) carried by physicians to workstations or mainframe computers with large storage capabilities. The healthcare providers 130 are equipped with computer systems 140 that store and process patient records 142. The manufacturer 132 has a computer system 144 that tracks device data 146 returned from ICTDs 102. The clinical groups 134 have computer systems 148 that store and analyze data across patient populations, as represented by a histogram 150. The regulatory agencies 136 maintain computer systems 152 that register and track healthcare risk data 154 for ICTDs.

The network architecture 100 supports two-way communication. Not only is data collected from the ICTD 102 and distributed to the various computer systems of the knowledge workers, but also information can be returned from these computer systems to the networked programmer 114 and/or the local transceiver 112 for communication back to the ICTD 102. Information returned to the ICTD 102 may be used to adjust operation of the device, or modify therapies being applied by the device. Such information may be imparted to the ICTD 102 automatically, without the patient's knowledge.

Additionally, information may be sent to a patient notification device 160 to notify the patient of some event or item. The patient notification device 160 can be implemented in a number of ways including, for example, as a telephone, a cellular phone, a pager, a PDA (personal digital assistant), a dedicated patient communication device, a computer, an alarm, and so on. Notifications may be as simple as an instruction to sound an alarm to inform the patient to call into the healthcare providers, or as complex as HTML-based pages with graphics and textual data to educate the patient. Notification messages sent to the patient notification device 160 can contain essentially any type of information related to cardiac medicinal purposes or device operation. Such information might include new studies released by clinical groups pertaining to device operation and patient activity (e.g., habits, diets, exercise, etc.), recall notices or operational data from the manufacturer, patient-specific instructions sent by the healthcare providers, or warnings published by regulatory groups.

Notifications can be sent directly from the knowledge worker to the patient. Additionally, the network architecture 100 may include a notification system 170 that operates computer systems 172 designed to create and deliver notification messages 174 on behalf of the knowledge workers. The notification system 170 delivers the messages in formats supported by the various types of patient notification devices 160. For instance, if the patient carries a pager, a notification message might consist of a simple text statement in a pager protocol. For a more sophisticated wireless-enabled PDA or Internet-oriented cellular phone, messages might contain more than text data and be formatted using WAP formats.

Figure 2:
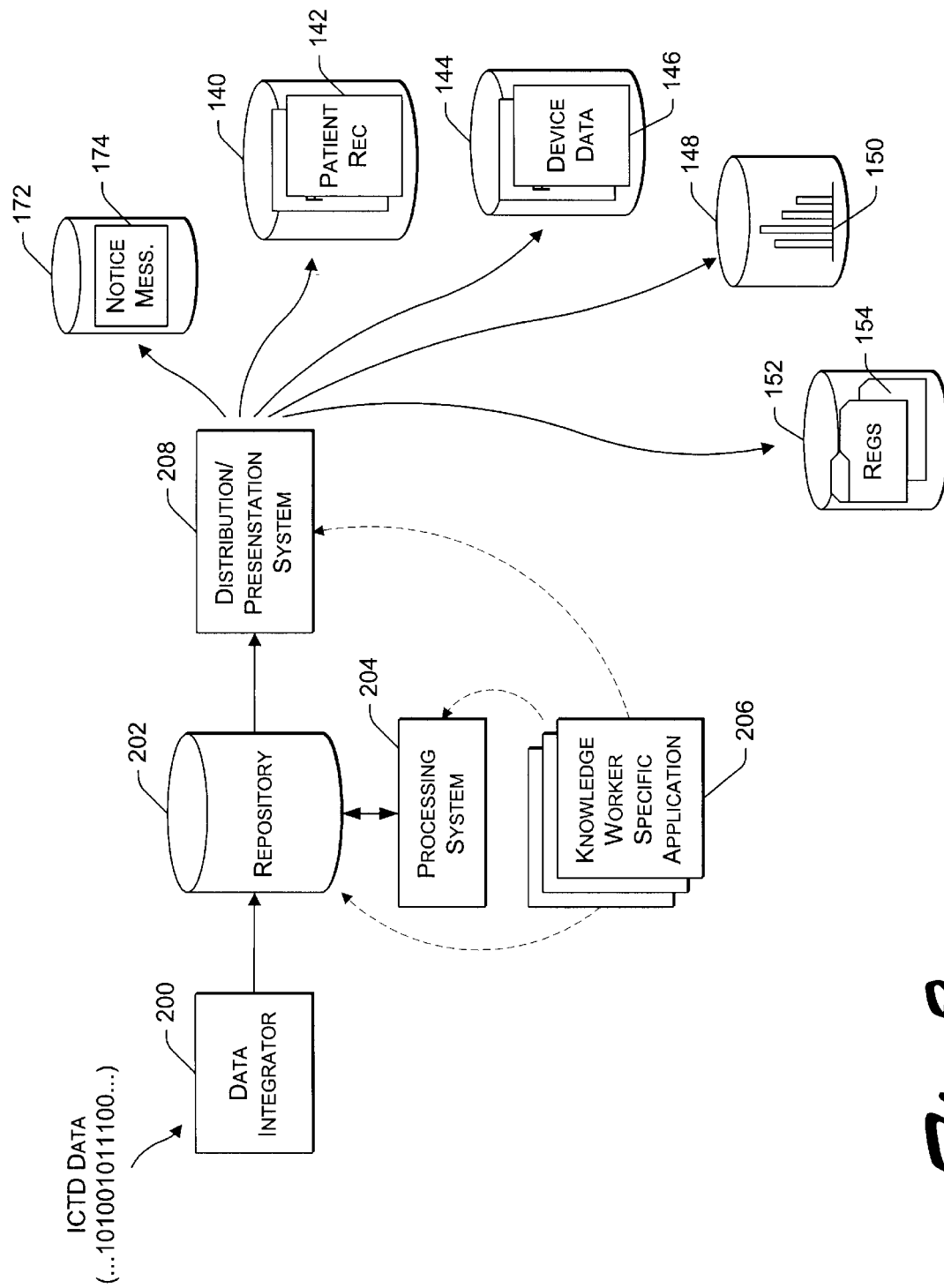
FIG. 2 is a functional diagram illustrating information flow from the ICTD to the computing systems associated with the knowledge workers.

FIG. 2 shows the flow of data from the implantable cardiac therapy device 102 to the various computer systems used by the knowledge workers. Data from the ICTD is output as digital data, as represented by the string of 0's and 1's. The data may consist of any number of items, including heart activity (e.g., ECG), patient information, device operation, analysis results from on-device diagnostics, and so on.

A data integrator 200 accumulates the data and stores it in a repository 202. A processing system 204 processes portions of the data according to various applications 206 that are specifically tailored to place the data into condition for various knowledge workers. For example, healthcare workers might be interested in certain portions of the data, such as the ECG data and the patient information. Clinical scientists might be interested in the heart data, but do not wish to see any patient information. Manufacturers may be interested in the raw data stream itself as a tool to discern how the device is operating. Depending on the needs of the end worker, the processing system 204 takes the raw device data, evaluates its accuracy and completeness, and generates different packages of data for delivery to the various knowledge workers. The processed data packages are also stored in the repository 202.

When the data is ready for delivery, a distribution/presentation system 208 distributes the different packages to the appropriate computer systems 140, 144, 148, 152, and 172. The distribution/presentation system 208 is configured to serve the packages according to the protocols and formats desired by the computer systems. In this manner, the network architecture 100 allows relevant portions of device data, collected from the ICTD, to be disseminated to the appropriate knowledge workers in a form they prefer.

Once the ICTD data is delivered, the computer systems 140, 144, 148, 152, and 172 store the data and/or present the data to the knowledge worker. The computer systems may perform further processing specific to their use of the data. Through these processes, the knowledge workers create additional information that is useful to the patient, or other knowledge workers with interests in ICTDs. For example, from the ICTD data, the knowledge workers might devise improved therapies for a given patient, or create instructions to modify operation of a specific ICTD, or gain a better understanding of how implantable cardiac devices operate in general, or develop better technologies for future generations of ICTDs. Much of this created knowledge can be shared among the various knowledge workers.

Figure 3:
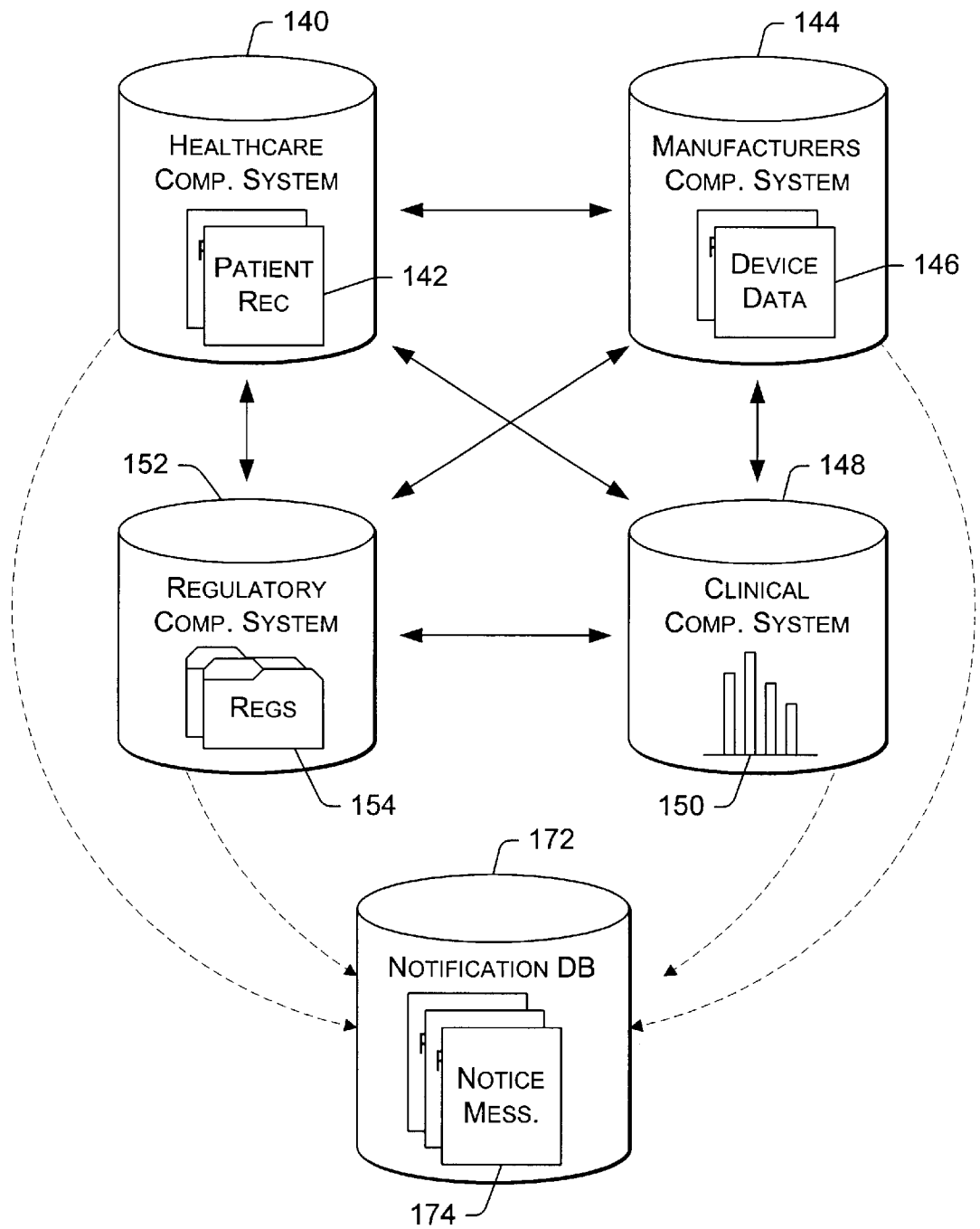
FIG. 3 is a functional diagram illustrating how the various computing systems share pieces of information to improve care given to the patient.

FIG. 3 shows how the various computing systems 140, 144, 148, 152, and 172 can cooperate and share pieces of information to improve the care given to a patient. Where appropriate and legally acceptable, the computer systems may be configured to pass non-private information among the various knowledge workers to better improve their understanding of the implantable medical field. Clinical results 150 produced by the clinical computer systems 148 may be shared with healthcare providers to improve patient care or with manufacturers to help in their design of next generation devices. The sharing of information may further lead to better and timelier healthcare for the patients.

If the collective knowledge base produces information that may prove helpful to the patient, that information can be passed to the notification system 172 for delivery to one or more patients. Also, any one of the knowledge workers may wish to employ the notification system 172 to send messages to the patient(s).

Figure 4:
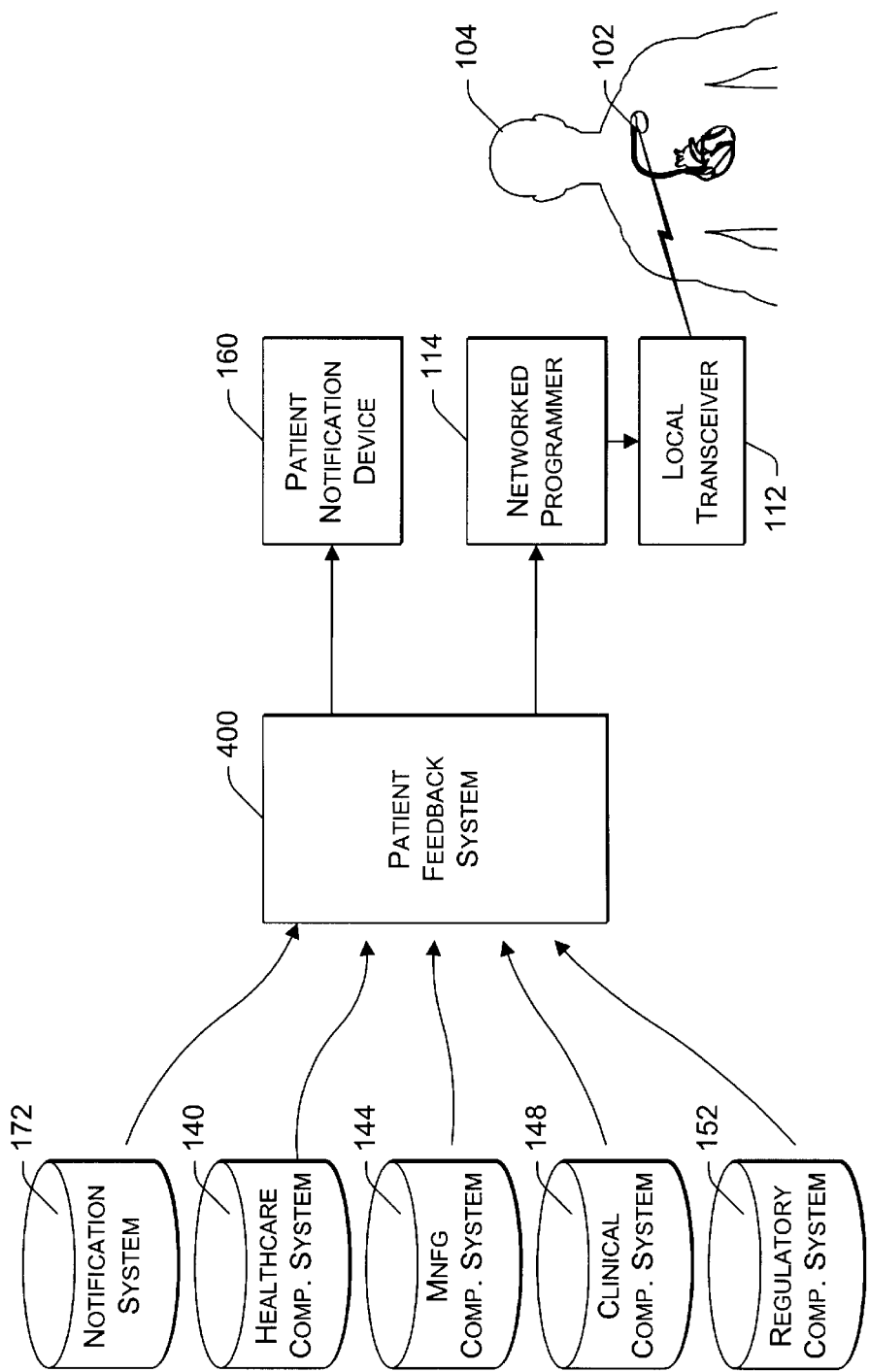
FIG. 4 is a functional diagram illustrating information flow from the computing systems back to the ICTD.

FIG. 4 shows, in more detail, the flow of information back from the various computer systems used by the knowledge workers to the implantable cardiac therapy device 102 or the patient notification device 160. Information from any one of the computing systems—healthcare computer system(s) 140, manufacturer computer system(s) 144, clinical computer system(s) 148, regulatory computer system(s) 152—or the notification system 172 can be sent to a patient feedback system 400. The patient feedback system 400 facilitates delivery of the information back to the patient. It may be an independent system, or incorporated into one or more of the computing. It may alternatively be integrated into the notification system 172.

The patient feedback system 400 may be implemented in many ways. As one exemplary implementation, the patient feedback system 400 is implemented as a server that serves content back to the networked programmer 114, which then uses the information to program the ICTD 102 through a built in transceiver 116, local transceiver 112, or wand-based telemetry. As another possible implementation, the patient feedback system may be a cellular or RF transmission system that sends information back to the patient feedback device 160.

The network architecture 100 facilitates continuous care around the clock, regardless of where the patient is located. For instance, suppose the patient is driving in the car when a cardiac episode occurs. The ICTD 102 detects the condition and transmits an alert message about the condition to the local transceiver 112. The message is processed and delivered to a physician's computer or PDA via the network 120. The physician can make a diagnosis and send some instructions back to the patient's ICTD. The physician might also have a notification message that guides the patient to a nearest healthcare facility for further treatment sent via the notification system 170 to the patient's notification device 160. Concurrently, the physician can share the patient's records online with an attending physician at the healthcare facility so that the attending physician can review the records prior to the patient's arrival.

Exemplary ICTD

Figure 5:
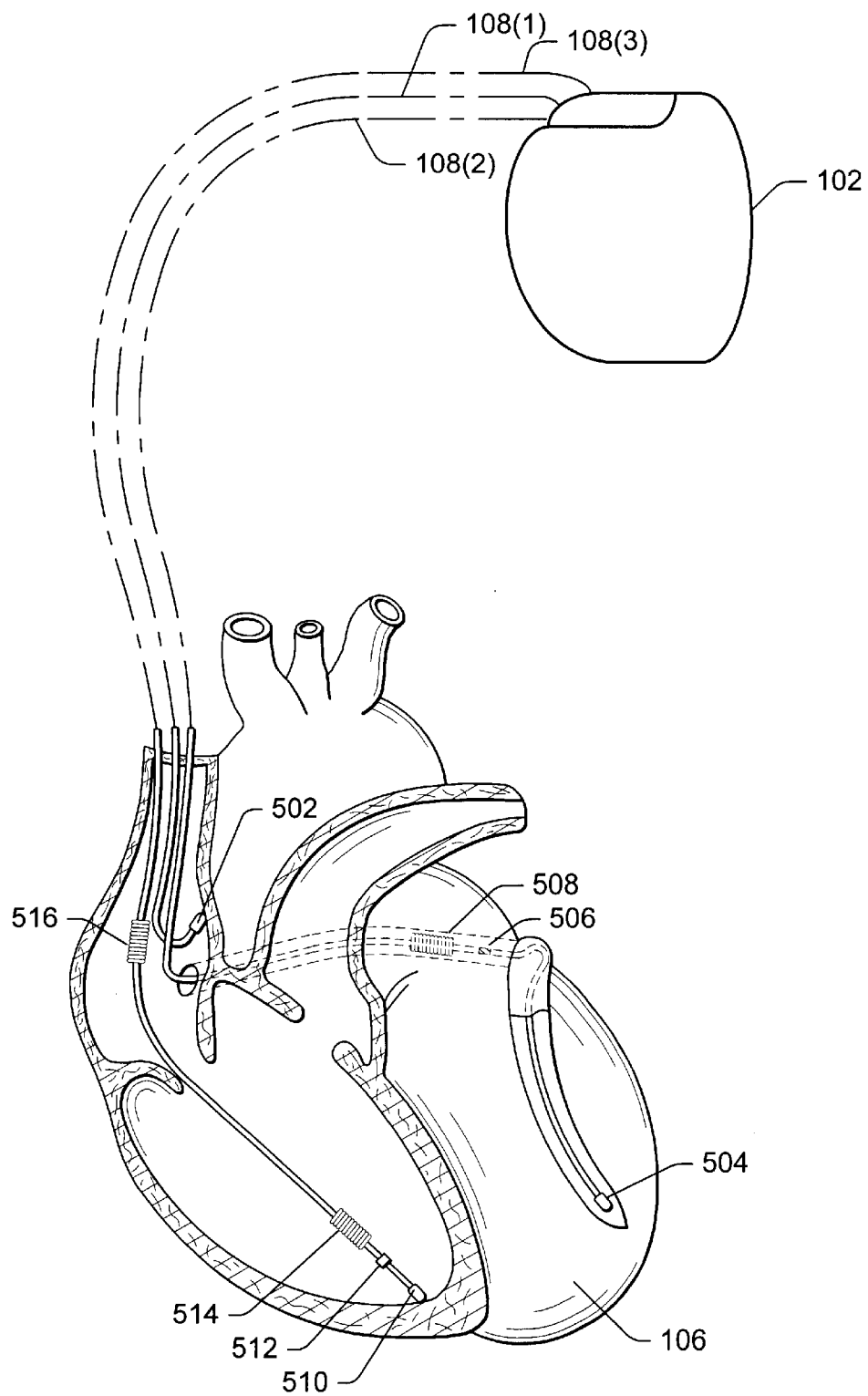
FIG. 5 is a simplified illustration of an ICTD in electrical communication with a patient's heart for monitoring heart activity and/or delivering stimulation therapy.

FIG. 5 shows an exemplary ICTD 102 in electrical communication with a patient's heart 106 for monitoring heart activity and/or delivering stimulation therapy, such as pacing or defibrillation therapies. The ICTD 102 is in electrical communication with a patient's heart 106 by way of three leads 108(1)–(3). To sense atrial cardiac signals and to provide right atrial chamber stimulation therapy, the ICTD 102 is coupled to an implantable right atrial lead 108(1) having at least an atrial tip electrode 502, which typically is implanted in the patient's right atrial appendage. To sense left atrial and ventricular cardiac signals and to provide left chamber pacing therapy, the ICTD 102 is coupled to a coronary sinus lead 108(2) designed for placement in the coronary sinus region via the coronary sinus. The coronary sinus lead 108(2) positions a distal electrode adjacent to the left ventricle and/or additional electrode(s) adjacent to the left atrium. An exemplary coronary sinus lead 108(2) is designed to receive atrial and ventricular cardiac signals and to deliver left ventricular pacing therapy using at least a left ventricular tip electrode 504, left atrial pacing therapy using at least a left atrial ring electrode 506, and shocking therapy using at least a left atrial coil electrode 508.

The ICTD 102 is also shown in electrical communication with the patient's heart 106 by way of an implantable right ventricular lead 108(3) having, in this implementation, a right ventricular tip electrode 510, a right ventricular ring electrode 512, a right ventricular (RV) coil electrode 514, and an SVC coil electrode 516. Typically, the right ventricular lead 108(3) is transvenously inserted into the heart 102 to place the right ventricular tip electrode 510 in the right ventricular apex so that the RV coil electrode 514 will be positioned in the right ventricle and the SVC coil electrode 516 will be positioned in the superior vena cava. Accordingly, the right ventricular lead 108(3) is capable of receiving cardiac signals, and delivering stimulation in the form of pacing and shock therapy to the right ventricle.

Figure 6:
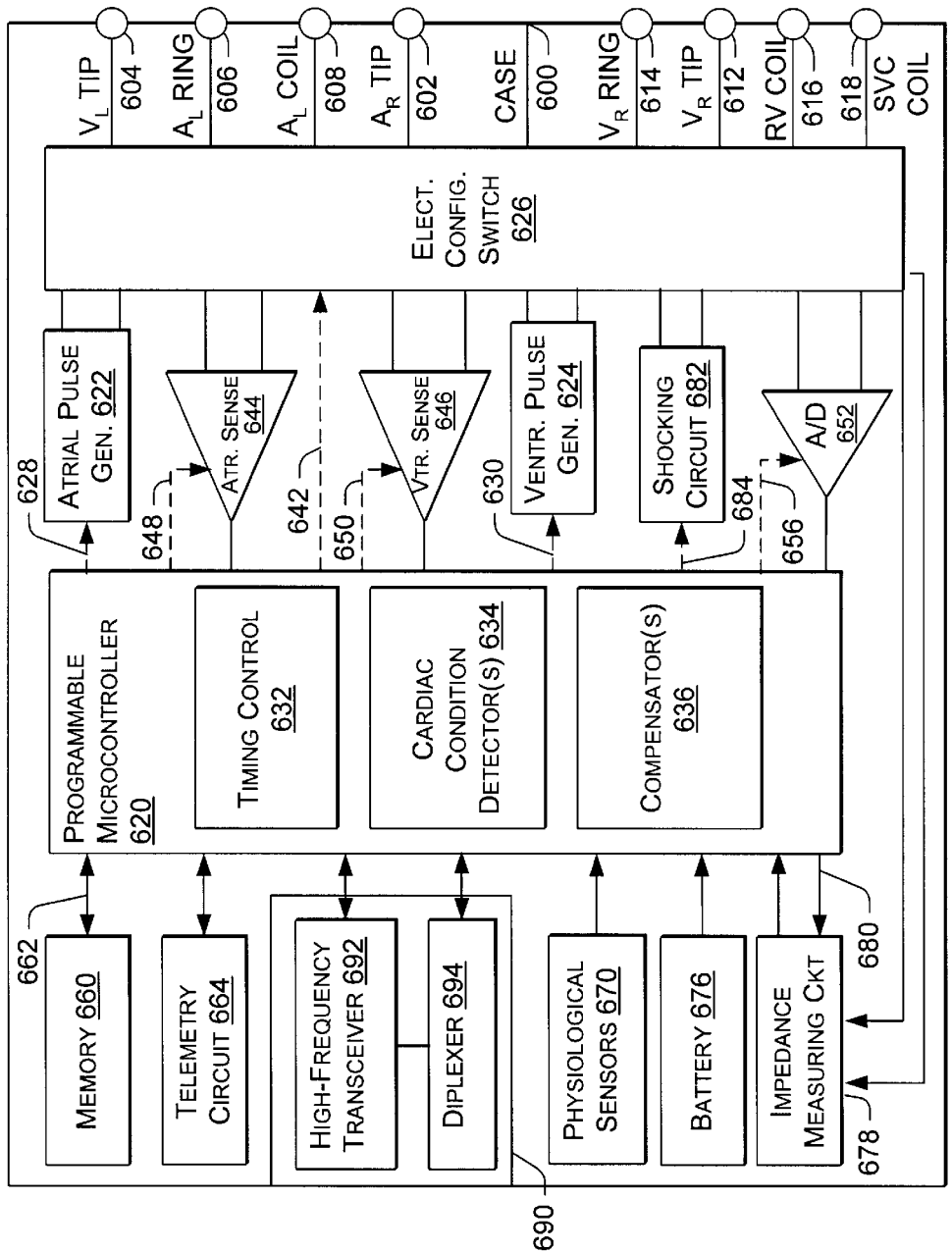
FIG. 6 is a functional block diagram of an exemplary implantable cardiac therapy device.

FIG. 6 shows an exemplary, simplified block diagram depicting various components of the ICTD 102. The ICTD 102 can be configured to perform one or more of a variety of functions including, for example, monitoring heart activity, monitoring patient activity, and treating fast and slow arrhythmias with stimulation therapy that includes cardioversion, defibrillation, and pacing stimulation. While a particular multi-chamber device is shown, it is to be appreciated and understood that this is done for illustration purposes.

The circuitry is housed in housing 600, which is often referred to as the "can", "case", "encasing", or "case electrode", and may be programmably selected to act as the return electrode for unipolar modes. Housing 600 may further be used as a return electrode alone or in combination with one or more of the coil electrodes for shocking purposes. Housing 600 further includes a connector (not shown) having a plurality of terminals 602, 604, 606, 608, 612, 614, 616, and 618 (shown schematically and, for convenience, the names of the electrodes to which they are connected are shown next to the terminals).

To achieve right atrial sensing and pacing, the connector includes at least a right atrial tip terminal ($A_R$ TIP) 602 adapted for connection to the atrial tip electrode 502. To achieve left chamber sensing, pacing, and shocking, the connector includes at least a left ventricular tip terminal ($V_L$ TIP) 604, a left atrial ring terminal ($A_L$ RING) 606, and a left atrial shocking terminal ($A_L$ COIL) 608, which are adapted for connection to the left ventricular ring electrode 504, the left atrial ring electrode 506, and the left atrial coil electrode 508, respectively. To support right chamber sensing, pacing, and shocking, the connector includes a right ventricular tip terminal ($V_R$ TIP) 612, a right ventricular ring terminal ($V_R$ RING) 614, a right ventricular shocking terminal (RV COIL) 616, and an SVC shocking terminal (SVC COIL) 618, which are adapted for connection to the right ventricular tip electrode 510, right ventricular ring electrode 512, the RV coil electrode 514, and the SVC coil electrode 516, respectively.

At the core of the ICTD 102 is a programmable microcontroller 620 that controls various operations of the ICTD, including cardiac monitoring and stimulation therapy. Microcontroller 620 includes a microprocessor (or equivalent control circuitry), RAM and/or ROM memory, logic and timing circuitry, state machine circuitry, and I/O circuitry.

Microcontroller 620 includes the ability to process or monitor input signals (data) as controlled by a program code stored in a designated block of memory. Any suitable microcontroller 620 may be used. The use of microprocessor-based control circuits for performing timing and data analysis functions are well known in the art.

For discussion purposes, microcontroller 620 is illustrated as including timing control circuitry 632 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, and so on. Microcontroller 220 may further include various types of cardiac condition detectors 634 (e.g., an arrhythmia detector, a morphology detector, etc.) and various types of compensators 636 (e.g., orthostatic compensator, syncope response module, etc.). These components can be utilized by the device 102 for determining desirable times to administer various therapies. The components 632–636 may be implemented in hardware as part of the microcontroller 620, or as software/firmware instructions programmed into the device and executed on the microcontroller 620 during certain modes of operation.

The ICTD 102 further includes an atrial pulse generator 622 and a ventricular pulse generator 624 that generate pacing stimulation pulses for delivery by the right atrial lead 108(1), the coronary sinus lead 108(2), and/or the right ventricular lead 108(3) via an electrode configuration switch 626. It is understood that in order to provide stimulation therapy in each of the four chambers of the heart, the atrial and ventricular pulse generators, 622 and 624, may include dedicated, independent pulse generators, multiplexed pulse generators, or shared pulse generators. The pulse generators 622 and 624 are controlled by the microcontroller 620 via appropriate control signals 628 and 630, respectively, to trigger or inhibit the stimulation pulses.

The electronic configuration switch 626 includes a plurality of switches for connecting the desired electrodes to the appropriate I/O circuits, thereby providing complete electrode programmability. Accordingly, switch 626, in response to a control signal 642 from the microcontroller 620, determines the polarity of the stimulation pulses (e.g., unipolar, bipolar, combipolar, etc.) by selectively closing the appropriate combination of switches (not shown).

Atrial sensing circuits 644 and ventricular sensing circuits 646 may also be selectively coupled to the right atrial lead 108(1), coronary sinus lead 108(2), and the right ventricular lead 108(3), through the switch 626 to detect the presence of cardiac activity in each of the four chambers of the heart. Accordingly, the atrial (ATR. SENSE) and ventricular (VTR. SENSE) sensing circuits, 644 and 646, may include dedicated sense amplifiers, multiplexed amplifiers, or shared amplifiers. Each sensing circuit 644 and 646 may further employ one or more low power, precision amplifiers with programmable gain and/or automatic gain control, bandpass filtering, and a threshold detection circuit to selectively sense the cardiac signal of interest. The automatic gain control enables the ICTD 102 to deal effectively with the difficult problem of sensing the low amplitude signal characteristics of atrial or ventricular fibrillation. Switch 626 determines the "sensing polarity" of the cardiac signal by selectively closing the appropriate switches. In this way, the clinician may program the sensing polarity independent of the stimulation polarity.

The outputs of the atrial and ventricular sensing circuits 644 and 646 are connected to the microcontroller 620 which, in turn, is able to trigger or inhibit the atrial and ventricular pulse generators 622 and 624, respectively, in a demand fashion in response to the absence or presence of cardiac activity in the appropriate chambers of the heart. The sensing circuits 644 and 646 receive control signals over signal lines 648 and 650 from the microcontroller 620 for purposes of controlling the gain, threshold, polarization charge removal circuitry (not shown), and the timing of any blocking circuitry (not shown) coupled to the inputs of the sensing circuits 644 and 646.

Cardiac signals are also applied to inputs of an analog-to-digital (A/D) data acquisition system 652. The data acquisition system 652 is configured to acquire intracardiac electrogram signals, convert the raw analog data into a digital signal, and store the digital signals for later processing and/or telemetric transmission to an external device 654. The data acquisition system 652 is coupled to the right atrial lead 108(1), the coronary sinus lead 108(2), and the right ventricular lead 108(3) through the switch 626 to sample cardiac signals across any pair of desired electrodes.

The data acquisition system 652 may be coupled to the microcontroller 620, or other detection circuitry, to detect an evoked response from the heart 106 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 620 detects a depolarization signal during a window following a stimulation pulse, the presence of which indicates that capture has occurred. The microcontroller 620 enables capture detection by triggering the ventricular pulse generator 624 to generate a stimulation pulse, starting a capture detection window using the timing control circuitry 632 within the microcontroller 620, and enabling the data acquisition system 652 via control signal 656 to sample the cardiac signal that falls in the capture detection window and, based on the amplitude, determines if capture has occurred.

The microcontroller 620 is further coupled to a memory 660 by a suitable data/address bus 662, wherein the programmable operating parameters used by the microcontroller 620 are stored and modified, as required, in order to customize the operation of the implantable device 102 to suit the needs of a particular patient. Such operating parameters define, for example, pacing pulse amplitude, pulse duration electrode polarity, rate, sensitivity, automatic features, arrhythmia detection criteria, and the amplitude, waveshape and vector of each shocking pulse to be delivered to the patient's heart 106 within each respective tier of therapy. With memory 660, the ICTD 102 is able to sense and store a relatively large amount of data (e.g., from the data acquisition system 652), which may transmitted to the external network of knowledge workers for subsequent analysis.

Operating parameters of the ICTD 102 may be non-invasively programmed into the memory 660 through a telemetry circuit 664 in telemetric communication with an external device, such as a programmer 110 or local transceiver 112. The telemetry circuit 664 advantageously allows intracardiac electrograms and status information relating to the operation of the device 102 (as contained in the microcontroller 620 or memory 660) to be sent to the external devices.

The ICTD 100 can further include one or more physiologic sensors 670, commonly referred to as "rate-responsive" sensors because they are typically used to adjust pacing stimulation rate according to the exercise state of the patient. However, the physiological sensor 670 may further be used to detect changes in cardiac output, changes in the physiological condition of the heart, or diurnal changes in activity (e.g., detecting sleep and wake states, detecting position or postural changes, etc.). Accordingly, the microcontroller 620 responds by adjusting the various pacing parameters (such as rate, AV Delay, V—V Delay, etc.) at which the atrial and ventricular pulse generators, 622 and 624, generate stimulation pulses. While shown as being included within the device 102, it is to be understood that the physiologic sensor 670 may also be external to the device 102, yet still be implanted within or carried by the patient. Examples of physiologic sensors that may be implemented in device 102 include known sensors that, for example, sense respiration rate and/or minute ventilation, pH of blood, ventricular gradient, and so forth.

The ICTD 102 additionally includes a battery 676 that provides operating power to all of circuits shown in FIG. 2. If the device 102 is configured to deliver pacing or shocking therapy, the battery 676 is capable of operating at low current drains for long periods of time (e.g., preferably less than 10 $\mu$A), and is capable of providing high-current pulses (for capacitor charging) when the patient requires a shock pulse (e.g., preferably, in excess of 2 A, at voltages above 2 V, for periods of 10 seconds or more). The battery 676 also desirably has a predictable discharge characteristic so that elective replacement time can be detected. As one example, the device 102 employs lithium/silver vanadium oxide batteries.

The ICTD 102 can further include magnet detection circuitry (not shown), coupled to the microcontroller 620, to detect when a magnet is placed over the device 102. A magnet may be used by a clinician to perform various test functions of the device 102 and/or to signal the microcontroller 620 that the external programmer is in place to receive or transmit data to the microcontroller 620 through the telemetry circuits 664.

The ICTD 102 further includes an impedance measuring circuit 678 that is enabled by the microcontroller 620 via a control signal 680. Uses for an impedance measuring circuit 678 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 678 is advantageously coupled to the switch 626 so that any desired electrode may be used.

In the case where the device 102 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 620 further controls a shocking circuit 682 by way of a control signal 684. The shocking circuit 682 generates shocking pulses of low (up to 0.5 Joules), moderate (0.5–10 Joules), or high energy (11 to 40 Joules), as controlled by the microcontroller 620. Such shocking pulses are applied to the patient's heart 106 through at least two shocking electrodes, and as shown in this implementation, selected from the left atrial coil electrode 508, the RV coil electrode 514, and/or the SVC coil electrode 516. As noted above, the housing 600 may act as an active electrode in combination with the RV coil electrode 514, or as part of a split electrical vector using the SVC coil electrode 516 or the left atrial coil electrode 508 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 620 is capable of controlling the synchronous or asynchronous delivery of the shocking pulses.

The ICTD 102 is further designed with the ability to support high-frequency wireless communication, typically in the radio frequency (RF) range. The ICTD 102 is equipped with a high-frequency transceiver 692 and a diplexer 694. High-frequency signals received by a dedicated antenna, or via leads 108, are passed to the transceiver 692 directly, or via diplexer 694. The high-frequency transceiver 692 may be configured to operate on one or a few frequencies, or may include a tuner that tunes to various frequencies when communicating with an external communication device (e.g., programmer, local transceiver, etc.).

In one implementation, the high-frequency circuitry may be contained within a secondary, isolated casing 690 to enable handling of high-frequency signals in isolation from the cardiac therapy circuitry. In this manner, the high-frequency signals can be safely received and transmitted, thereby improving telemetry communication, without adversely disrupting operation of the other device circuitry.

Exemplary Computing Device

Figure 7:
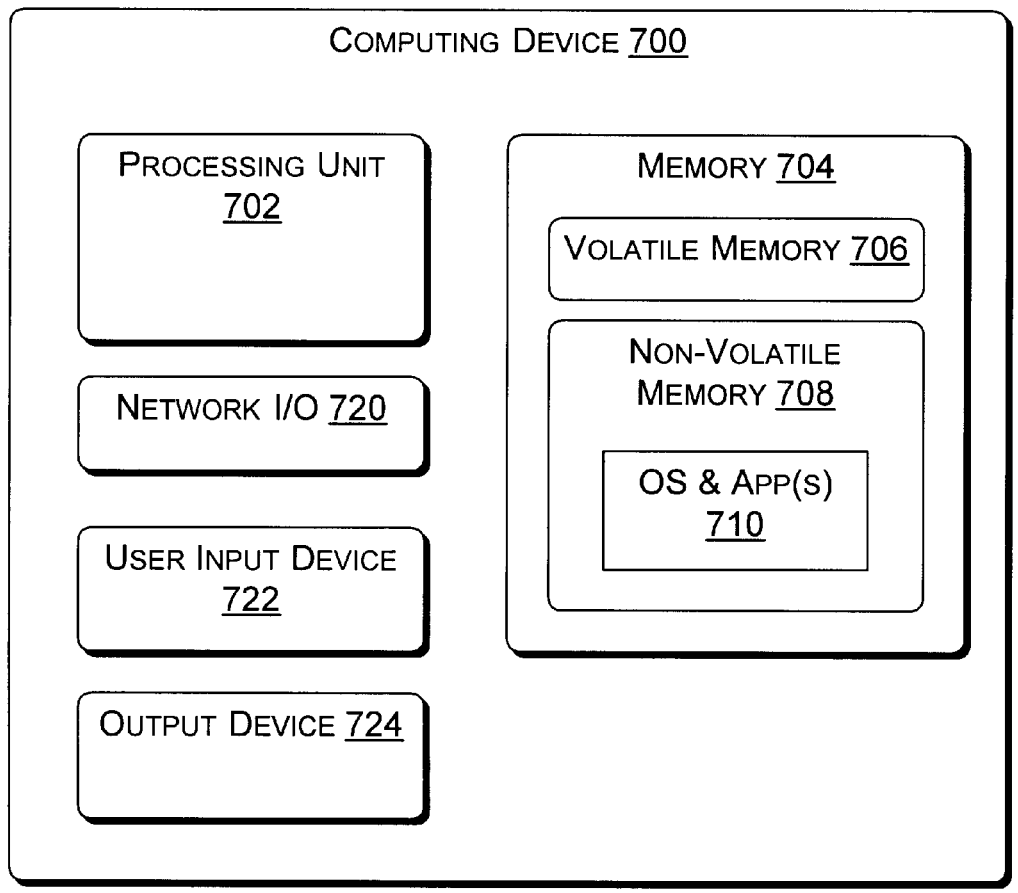
FIG. 7 is a functional block diagram of an exemplary computing device that may be used in the computing systems of the cardiac therapy network architecture.

FIG. 7 shows an exemplary computing device 700 employed in the computing systems of the cardiac therapy network architecture 100. It includes a processing unit 702 and memory 704. Memory 704 includes both volatile memory 706 (e.g., RAM) and non-volatile memory 708 (e.g., ROM, EEPROM, Flash, disk, optical discs, persistent storage, etc.). An operating and system and various application programs 710 are stored in non-volatile memory 708. When a program is running, various instructions are loaded into volatile memory 706 and executed by processing unit 702. Examples of possible applications that may be stored and executed on the computing device include the knowledge worker specific applications 206 shown in FIG. 2.

The computing device 700 may further be equipped with a network I/O connection 720 to facilitate communication with a network. The network I/O 720 may be a wire-based connection (e.g., network card, modem, etc.) or a wireless connection (e.g., RF transceiver, Bluetooth device, etc.). The computing device 700 may also include a user input device 722 (e.g., keyboard, mouse, stylus, touch pad, touch screen, voice recognition system, etc.) and an output device 724 (e.g., monitor, LCD, speaker, printer, etc.).

Various aspects of the methods and systems described throughout this disclosure may be implemented in computer software or firmware as computer-executable instructions. When executed, these instructions direct the computing device (alone, or in concert with other computing devices of the system) to perform various functions and tasks that enable the cardiac therapy network architecture 100.

Magnetic Coupling Antennas

One feature of the network architecture is an improved transmission range between the ICTD 102 and an external device such as the offline programmer 110 or the local transceiver 112. Long range telemetry allows communication with implanted medical devices at distances greater than conventional "wand telemetry" of a few inches. Longer range telemetry is made possible by employing high-frequency signals, such as RF signals. However, use of high-frequency transmissions introduces new challenges regarding how to effectively capture such transmissions and extract the data without disrupting operation of the cardiac therapy circuitry.

Generally, high-frequency transmission requires antennas of a certain length. One solution is to use a dedicated antenna. Such an antenna may be mounted in the header or constructed as part of the can. The challenge for this solution is that the size of the antenna is constrained by the volume available in the header or size of the can. As the devices are minimized, there is little room to locate a sizeable antenna. Another solution is to use one or more of the leads 108(1)–(3). Such leads are typically long enough to support RF transmission. For example, leads are often 60 cm in length, which is half a wavelength in air of an RF of approximately 250 MHz. The challenge for this arrangement is how to extract the high-frequency signals from leads that are also used to carry low frequency signals indicative of heart activity.

Regardless of which type of antenna is used, there is an additional challenge of isolating the high-frequency signals from the monitoring and stimulation circuitry. The leads 108(1)–(3) are connected to the device circuitry by way of a semi-transparent molded medium, sometimes known as a "header", and a ceramic-to-metal plug, known as a "feedthrough". The feed-through is a non-conductive orifice in the metal enclosure through which conductors pass through from the header into the interior of the can. Protective components are typically added to the feed-through to attenuate electromagnetic interference from entering the can and thereby protect the internal device electronics. In one common implementation, small capacitors of discoidal or other construction connect each conductor to a metal flange of the feed-through. The metal flange is electrically connected to the metal enclosure. The capacitors divert high frequency alternating current from the leads to the enclosure, and hence reduce the amount entering the electronic circuits.

Unfortunately, this is a symmetrical effect: the capacitors divert RF current that may be intentionally generated by the device electronics, such as for communication. Thus, it is difficult to effect RF communication by passing current through the feed-through.

As a result, the implantable device 102 used in the network system is constructed with structures that effectively extract the high-frequency data from the antenna and concurrently prevent high-frequency emanations from entering the can. The structures transfer electromagnetic energy between the internal device circuitry and the external antenna. Two structures are disclosed for purposes of illustration: a toroid-coupled lead antenna and an inductive feed-through. Other constructions that conform to the principles described with respect to these structures may also be employed.

Toroid-Coupled Lead Antenna

Figure 8:
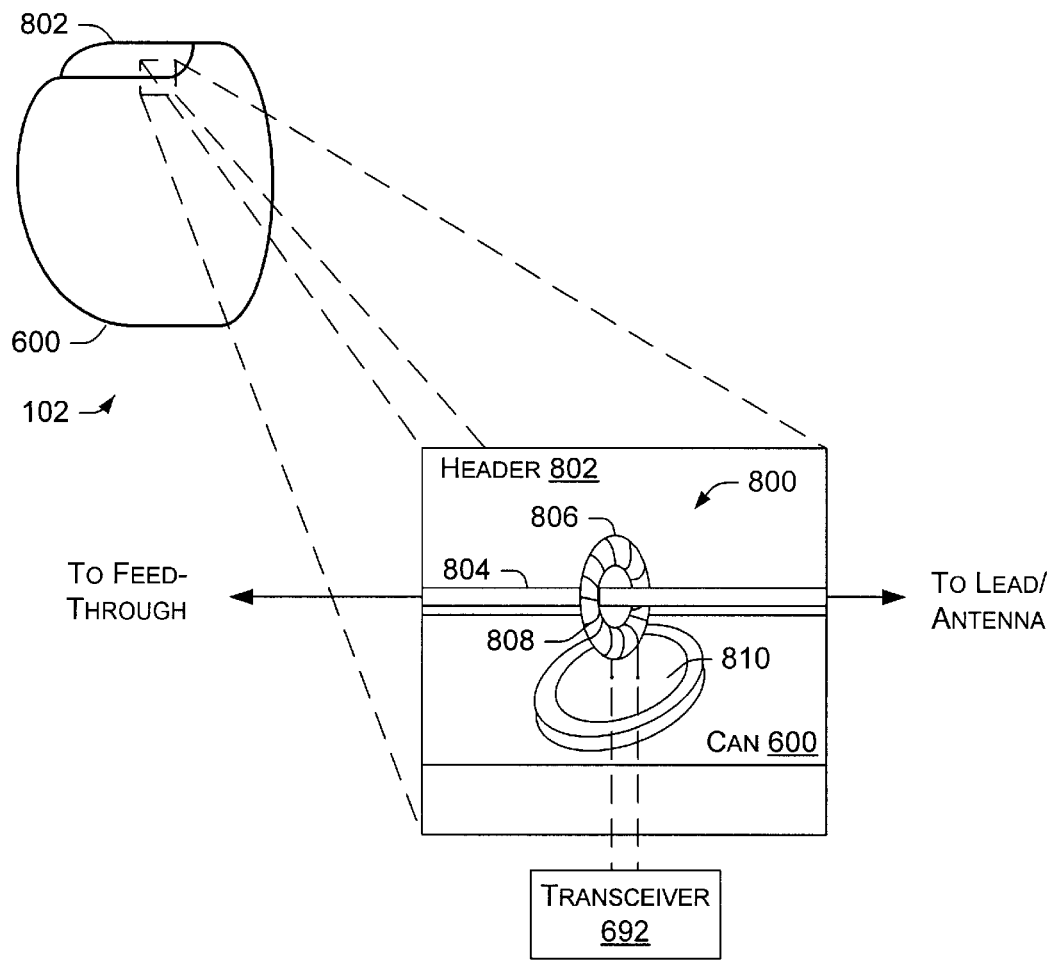
FIG. 8 is a diagrammatic illustration of an ICTD with an exploded sectional view of a first implementation of a magnetic coupling antenna structure.

FIG. 8 shows an ICTD 102 that employs a toroid-coupled lead antenna 800 as a way to capture communication signals conducted on one or more leads 108 or a dedicated antenna. The ICTD has a header 802 mounted on the can 600 to interface with the sensing/stimulation leads 108(1)–(3) attached to the heart (FIG. 5). The can is made, for example, of a metallic material (e.g., titanium) and the header is formed of a modeled, non-conductive material (e.g., epoxy).

In the exploded view of FIG. 8, the toroid-coupled lead antenna 800 includes a conductor 804 having one end electrically coupled to a sensing/stimulation lead 108. In this way, the lead essentially serves as an antenna for high-frequency communication. This first end of the conductor may alternatively be coupled to a dedicated antenna. The other end of conductor 804 is electronically coupled to the circuitry via a feed-through (not shown) and hence makes contact, directly or indirectly, with the metal enclosure 600. Indirect contact is accomplished by way of a small capacitor, such as a discoidal capacitor.

The also includes a toroidally-shaped member 806 having an aperture through which the conductor 804 is passed. In the illustrated implementation, the toroidally-shaped member 806 is oriented perpendicular to the longitudinal axis of the conductor 804. The small toroidally-shaped member 806 is formed of resistive magnetic material, such as ferrite. A winding 808 is formed by several turns of the same conductive wire on the toroidally-shaped member 806. The two ends of the winding are conveyed through a non-conductive feed-through 810 to the transceiver 692 inside the can 600.

The toroidal turns of wire 808 on magnetic member 806 forms a primary winding of a transformer. A secondary winding of the transformer is formed as a single turn radiation loop completed by a conducting path through conductor 804, sensing/stimulation lead 108, tissue stimulating electrode(s), the patient's tissue, the feedthrough discoidal capacitor, and the metal enclosure 600. The feedthrough capacitance reduces the impedance of the single turn secondary winding. The load for the secondary winding is the low tissue impedance of the patient's body and the feedthrough capacitance.

Radio frequency energy from a relatively high impedance source is supplied to the primary winding, and transformed into a high current low voltage source for the radiation loop. The current in the single turn secondary winding produces an RF magnetic field around the radiation loop, some of which emanates from the surface of the patient's body to facilitate radio wave propagation out to the external communication device.

The toroid-coupled lead antenna 800 allows long range RF communication using the pacing/sensing leads 108 as antennas, or a dedicated antenna. This eliminates the need to hold a programming wand within a few inches of the device. As a result, the long-range telemetry structure also enables transfer of RF current into the lead loop without having to couple through conventional feed-through capacitors.

Inductive Feed-Through

Figure 9:
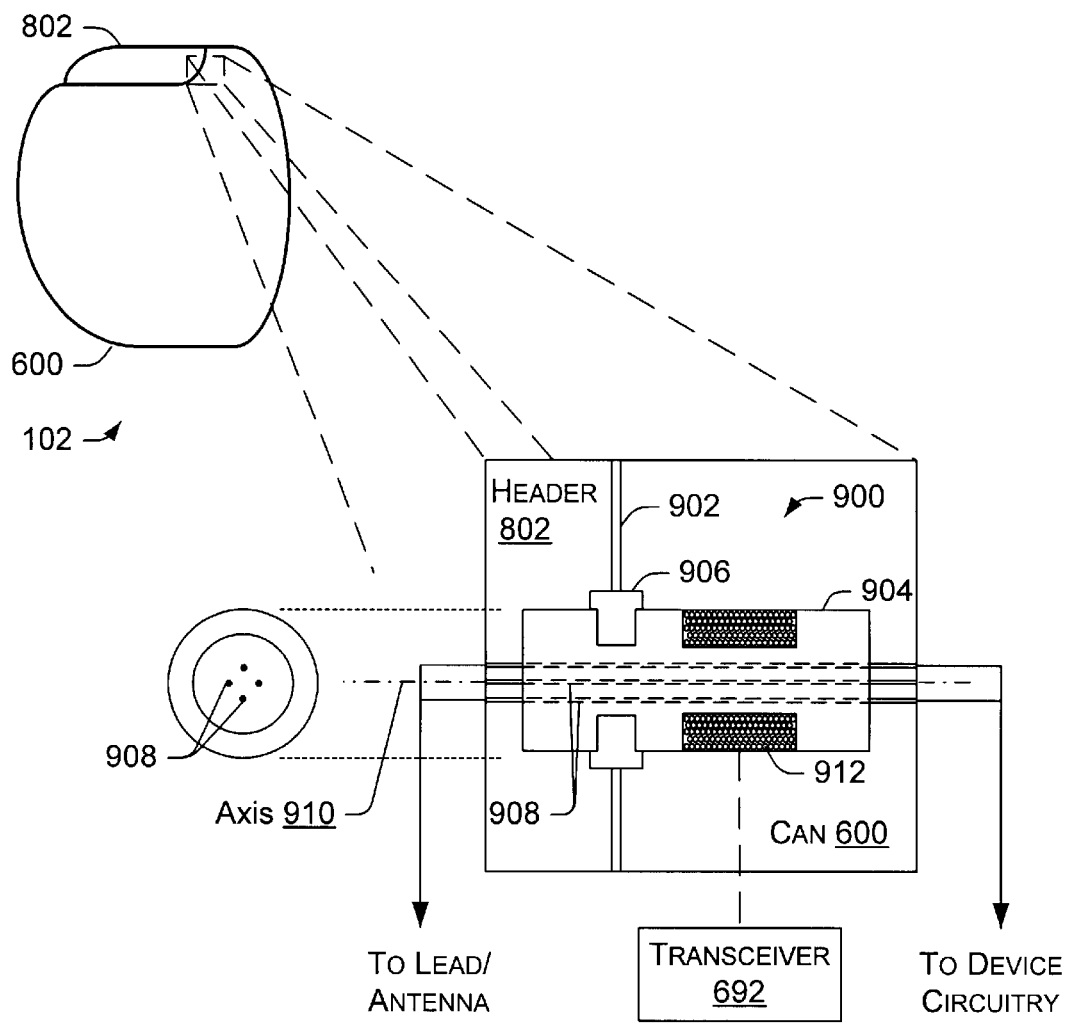
FIG. 9 is a diagrammatic illustration of an ICTD with an exploded sectional view of a second implementation of a magnetic coupling antenna structure.

FIG. 9 shows an ICTD 102 that employs an inductive feed-through 900 as a way to capture communication signals conducted on one or more leads 108 or a dedicated antenna. The feed-through 900 is illustrated in the exploded view as positioned within wall 902 of can 600. The feed-through 900 includes an elongated core 904 positioned in an aperture of the wall 902. The core 904 is made of a resistive magnetic material, such as ferrite (e.g., NnNiZn compounds). A collar 906 holds the core 904 in place in the wall aperture. The collar 906 is made of a non-conductive material (e.g., ceramic material, ferrite, ceramic/ferrite integration, etc.) to electrically insulate the core from the metal wall.

One or more conductors 908 traverse longitudinally along an axis 910 of the core 904. As illustrated in FIG. 9, four conductors 904 are spaced around the core center and run parallel along the longitudinal axis 910. The first ends of conductors 904 are coupled to one or more leads 108. The second ends of conductors 904 are coupled to the device circuitry inside the can 600. The conductors 908 carry signals indicative of cardiac activity as captured by the sensing electrodes. The conductors 908 might also carry stimulation pulses delivered to the lead 108.

A winding 912 is wound around core 904 on the interior side of the can wall 902. The winding 912 is oriented perpendicularly to the longitudinal axis 910 of the core 904. The winding 912 is coupled to the transceiver 692.

To enable communication, the inductive feed-through 900 produces a small scale, alternating magnetic field by passing a current through the winding 912 on the magnetic, resistive core 904. That is, current in the winding 912 produces an axially-directed magnetic field that "leaks" out of the wall 902 on the left hand side of collar 906. This field induces a magnetic influence which may be detected by a programming wand. Since the collar 906 is bounded by a circular metal perimeter of the can wall 902, the alternating nature of the magnetic field in the core 904 generates eddy currents in the metal perimeter. These eddy currents help propagate the influence of an electromagnetic field outside the device. Production of these eddy currents is aided by a transformer action resulting from a large number of turns of the coil winding 912 relative to a turn winding formed by the circular metal perimeter.

Incoming communication signals (high or low frequency) induce fluctuations in the magnetic field. Externally induced fluctuations are sensed and decoded by the transceiver 692 to extract information from the external communication device, such as queries or programming data. The transceiver 692 can also control the current flowing through the winding 912 to introduce magnetic fluctuations which propagate communication signals back out of the ICTD to the external communication device.

The orientation of the magnetic field is parallel to the core axis 910 and sensing conductors 908. As a result, there is no interruption of the sensed signals being carried on the sensing leads. Furthermore, since the magnetic core attenuates EMI on the conductors, the inductive feed-through 900 does not need to utilize feed-through capacitors.

Exemplary Packaging Design

The magnetic coupling antennas described above with respect to FIGS. 8 and 9 can be incorporated into many different types of implantable devices, including cardiac defibrillators and cardiac pacemakers. The magnetic coupling antennas may be used for both high-frequency and low-frequency transmissions. In the case of high-frequency transmission, however, there is an additional challenge of preventing high frequency signals from interfering with the device circuitry, such as the sensing and stimulation circuitry of an ICTD. The following description is directed to one possible device design that addresses this challenge.

Figure 10:
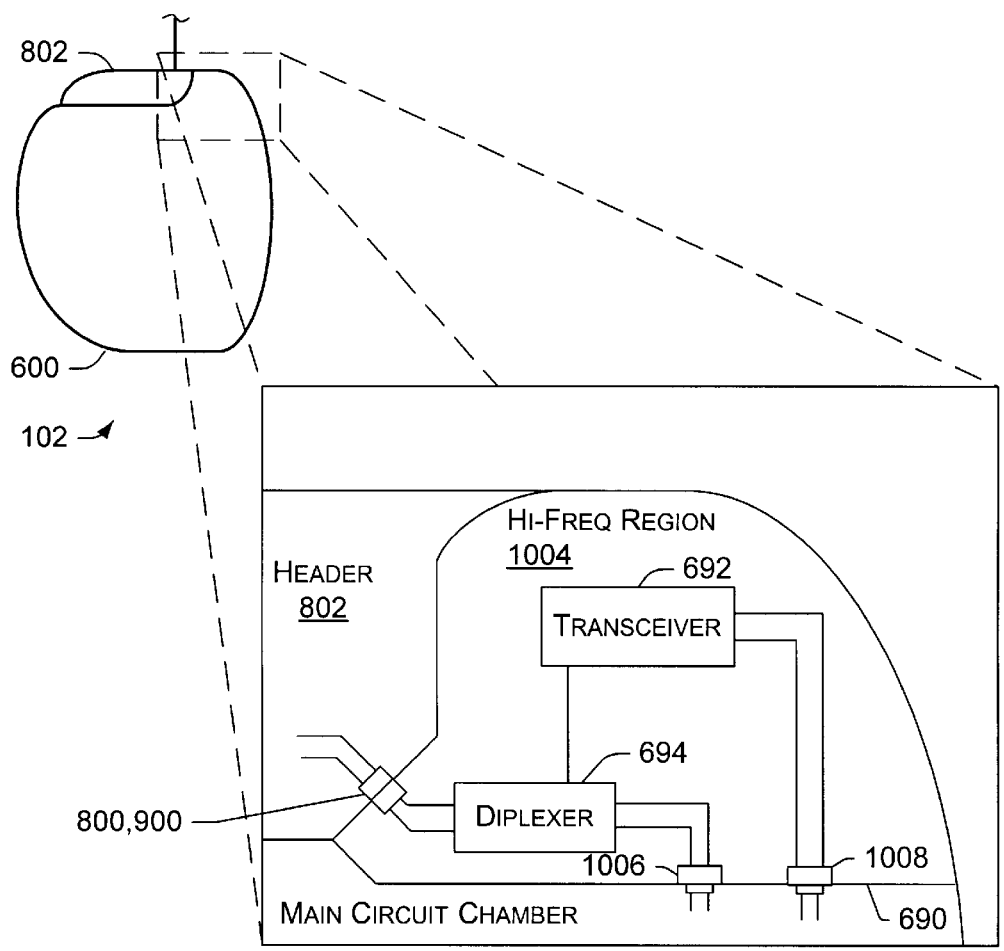
FIG. 10 is a diagrammatic illustration of an ICTD with packaging that defines dual isolated chambers, one for housing communication circuitry and a second for housing monitoring and stimulation circuitry.

FIG. 10 shows an exemplary ICTD 102 that is equipped with additional high-frequency packaging and circuitry to support long range telemetry. Generally, ICTD 102 is designed with a hermetically shielded can 600 to prevent electromagnetic interference (EMI) from disrupting operation of the sensing and/or stimulation circuitry. Conventional cans 600 are designed to prevent penetration of high frequencies, trying to limit communication to the low frequency ranges of less than 200 KHz.

As shown in FIG. 10, the ICTD can 600 is designed with a separate frequency-isolated packaging region 1004 adjacent to the header 802. The region 1004 is defined in part by wall 690, which is constructed, for example, of a conducting material such as titanium. The high-frequency packaging region 1004 can be thought of as a separate can or chamber that isolates the RF components from the main circuitry. The dual-can design enables the ICTD to handle high-frequency signals carrying data and control information in one can of the device without disrupting operation of the main circuitry in the second can or chamber of the device.

The transceiver 692 and diplexer 694 are positioned within the high-frequency packaging region 1004. Signals received from a lead 108 or a dedicated antenna are passed through the high-frequency packaging region 1004, where high-frequency signals are separated from low-frequency signals and handled in isolation from the device circuitry in the main chamber.

The magnetic coupling structures—toroid-coupled lead antenna 800 and inductive feed-through 900—may be positioned in the can 600 between the header 802 and high-frequency region 1104. Communication signals received via these structures are passed to the transceiver 692, while the cardiac signals are passed to the device circuitry in the main chamber via a conventional feed-through 1006. Another feed-through 1008 conducts data and power between the transceiver 692 and the device circuitry.

The dual-chamber design provides optimal isolation. The design isolates the main monitoring/stimulating circuitry from any RF interference emanated from the diplexer or transceiver, while simultaneously allowing long-range RF telemetry communication. Additionally, the design allows the leads to be used as both stimulation/sensing leads and as a radio frequency (RF) antenna, without causing interference to the monitoring and/or stimulation functions.

In the illustrated implementation, the high-frequency region 1004 is shown adjacent to header 802 and above the main circuit chamber, encapsulated by the outer can wall of the device and the interior wall 690. It is noted that the region 1004 may be located in any number of places. It may be, for example, implemented as an isolated cavity contained entirely within the main circuit chamber. Alternatively, it may be constructed external to the ICTD 102, but employ part of the exterior can 600 to define a portion of the region. Another possible implementation is to construct the high-frequency region as a separate implantable can that is in communication with the ICTD, but implanted apart from the ICTD 102.

Conclusion

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. An implantable medical device comprising:
   circuitry to process physiological signals carried on at least one lead;
   a transceiver to enable communication;
   a casing to hold the circuitry and the transceiver; and
   a magnetic coupling structure to transfer, via electromagnetic energy, communication signals between the lead and the transceiver.

2. An implantable medical device as recited in claim 1, wherein the magnetic coupling structure is positioned in an aperture of the casing to transfer the communication signals in and out of the casing.

3. An implantable medical device as recited in claim 1, further comprising a header mounted on the casing to interface with the leads, the magnetic coupling structure being positioned in the header.

4. An implantable medical device as recited in claim 1, wherein the magnetic coupling structure comprises:
   a toroid-shaped member with an opening;
   a conductor passing through the opening in the toroid-shaped member, the conductor being electrically coupled to the lead;
   a winding on the toroid-shaped member; and
   wherein the winding and a conductive path containing the conductor and the lead form a transformer that produces a magnetic field for transferring the communication signals.

5. An implantable medical device as recited in claim 4, wherein the toroid-shaped member is formed of a magnetic material.

6. An implantable medical device as recited in claim 4, wherein the transceiver is coupled to the winding.

7. An implantable medical device as recited in claim 1, wherein the magnetic coupling structure comprises:
   a core formed of magnetic material and positioned in an aperture in the casing;
   at least one conductor extending along a longitudinal axis of the core, the conductor being coupled to the lead; and
   a winding around the core and oriented perpendicularly to the longitudinal axis of the core.

8. An implantable medical device as recited in claim 7, wherein the core is formed of a magnetic material.

9. An implantable medical device as recited in claim 7, wherein the core attenuates interference on the conductor.

10. An implantable medical device as recited in claim 7, wherein the transceiver is coupled to the winding.

11. An implantable medical device as recited in claim 7, further comprising a ceramic collar to hold the core in the aperture of the casing.

12. An implantable medical device as recited in claim 1, wherein the casing houses the circuitry and the transceiver in separate chambers to isolate communication signals from interfering with the circuitry.

13. A network system comprising:
   an implantable medical device comprising,
   circuitry to process physiological signals carried on at least one lead;
   a transceiver to enable communication,
   a casing to hold the circuitry and the transceiver, and
   a magnetic coupling structure to transfer, via electromagnetic energy, communication signals between the lead and the transceiver; and
   a computing network to link one or more computing systems to the implantable medical device.

14. A structure for an implantable medical device, comprising:
   a magnetic member having an opening;
   a first conductor wound around the member;
   a second conductor extending through the opening in the magnetic member; and the first and second conductors forming respective primary and secondary windings of a transformer that produces a magnetic field to transfer communication signals into and out of the implantable medical device.

15. A structure as recited in claim 14, wherein the magnetic member is formed of a ferrite material.

16. A structure as recited in claim 14, wherein the second conductor is configured to connect to a sensing or stimulating lead of the implantable medical device.

17. A structure as recited in claim 14, wherein the second conductor extends along an axis and the magnetic member is oriented perpendicular to the axis.

18. A structure as recited in claim 14, wherein the magnetic member is toroid shaped.

19. A structure as recited in claim 14, wherein the magnetic member is configured to reside outside of a casing of the implantable medical device and the first conductor is passed through a feed-through into the casing.

20. A structure for an implantable medical device, the implantable medical device having a casing that houses device circuitry, the structure comprising:
   a core formed of magnetic material and positioned in an opening in the casing of the implantable medical device;
   at least one conductor extending along a longitudinal axis of the core; and
   a winding around the core and oriented perpendicularly to the longitudinal axis of the core so that passing current through the winding produces an electromagnetic field used in transferring communication signals into and out of the implantable medical device.

21. A structure as recited in claim 20, wherein the core is formed of a ferrite material.

22. A structure as recited in claim 20, wherein the core attenuates interference on the conductor.

23. A structure as recited in claim 20, wherein the winding resides inside of the casing.

24. A structure recited in claim 20, further comprising a non-conductive collar to mount the core within the opening of the casing.

25. A structure as recited in claim 20, wherein the magnetic field generates eddy currents in the casing that propagate the electromagnetic field outside of the implantable medical device.

26. A feed-through adapted for an implantable medical device comprising at least one conductor embedded substantially along an axis of a core, the core being formed of a magnetic material, the at least one conductor being coupled to a lead.

27. A feed-through as recited in claim 26, wherein the core is formed of a ferrite material.

28. A feed-through as recited in claim 26, further comprising a conductive winding wrapped around the core.

29. A feed-through as recited in claim 26, wherein the conductor is aligned along a longitudinal axis of the core and further comprising a conductive winding wrapped around the core.

30. An implantable medical device, comprising:
   processing means for processing physiological signals carried on one or more leads;
   communication means for enabling communication with a remote device; and
   magnetic coupling means for transferring, via electromagnetic energy, communication signals between at least one lead and the communication means.

31. An implantable medical device as recited in claim 30, wherein the communication means comprises an RF transceiver.

32. An implantable medical device as recited in claim 30, wherein the magnetic coupling means comprises:
   a magnetic annular member encircling the lead; and
   a winding on the magnetic annular member through which current is passed to produce the electromagnetic energy, and in which an electromotive force may be induced.

33. An implantable medical device as recited in claim 30, wherein the magnetic coupling means comprises:
   a core formed of magnetic material;
   at least one conductor extending along a longitudinal axis of the core, the conductor being coupled to the lead; and
   a winding around the core and oriented perpendicularly to the longitudinal axis of the core, the winding conducting current to produce the electromagnetic energy.

34. An implantable medical device as recited in claim 30, further comprising casing means for holding the processing means and the communication means in frequency isolation from one another to prevent the communication signals from interfering with the processing means.

35. A cardiac network system comprising:
   an implantable medical device comprising,
   processing means for processing physiological signals carried on one or more leads,
   communication means for enabling communication with a remote device, and
   magnetic coupling means for transferring, via electromagnetic energy, communication signals between at least one lead and the communication means; and
   a computing network to link one or more computing systems to the implantable medical device.

36. A system comprising:
   an implantable medical device equipped with communication circuitry and configured to be coupled to leads attached to a patient;
   an external communication device to communicate with the implantable medical device; and
   a magnetic coupling structure to transfer, via electromagnetic energy, communication signals between at least one lead and the communication circuitry of the implantable medical device to enable communication between the implantable medical device and the external communication device.

37. A system as recited in claim 36, wherein the implantable medical device comprises an implantable cardiac therapy device.

38. A system as recited in claim 36, wherein the external communication device comprises a programmer that is capable of programming the implantable medical device.

39. A system as recited in claim 36, wherein the implantable medical device comprises a casing to house the communication circuitry and the magnetic coupling structure is positioned in an aperture of the casing to transfer the communication signals in and out of the casing.

40. A system as recited in claim 36, wherein the implantable medical device comprises a casing to house the communication circuitry and a header mounted on the casing to interface with the leads, the magnetic coupling structure being positioned in the header.

41. A system as recited in claim 36, wherein the magnetic coupling structure comprises:
   a toroid-shaped member around the lead, the toroid-shaped member being formed of a magnetic material;
   a winding on the toroid-shaped member; and
   the winding and the lead forming a transformer that produces a magnetic field for transferring the communication signals.

42. A system as recited in claim 36, wherein the magnetic coupling structure comprises:
   a core formed of magnetic material and positioned as a feed-through into the casing;
   at least one conductor extending along a longitudinal axis of the core, the conductor being coupled to the lead; and
   a winding around the core and oriented perpendicularly to the longitudinal axis of the core.

43. A network system comprising:

an implantable medical device equipped with communication circuitry and configured to be coupled to at least one lead attached to a patient, the implantable medical device having a magnetic coupling structure to transfer, via electromagnetic energy, communication signals between the lead and the communication circuitry;

an external communication device to communicate with the implantable medical device; and a computing network linking one or more computing systems with the external communication device to process data received from the implantable medical device.

44. A network system as recited in claim 43, wherein the magnetic coupling structure comprises:

a toroid-shaped member around the lead, the toroid-shaped member being formed of a magnetic material;

a winding on the toroid-shaped member; and the winding and the lead forming a transformer that produces a magnetic field for transferring the communication signals.

45. A network system as recited in claim 43, wherein the magnetic coupling structure comprises:

a core formed of magnetic material and positioned as a feed-through into the casing;

at least one conductor extending along a longitudinal axis of the core, the conductor being coupled to the lead; and a winding around the core and oriented perpendicularly to the longitudinal axis of the core.

* * * * *